US006348335B1

(12) United States Patent
Jaeger

(10) Patent No.: US 6,348,335 B1
(45) Date of Patent: *Feb. 19, 2002

(54) LOW-MOLECULAR ACTIVE WEIGHT INGREDIENT EXTRACT FROM YEASTS AND METHOD FOR PRODUCING IT

(75) Inventor: Christa Jaeger, Lucern (CH)

(73) Assignee: Thymopharma, AG, Lucern (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/644,565

(22) Filed: Aug. 24, 2000

Related U.S. Application Data

(62) Division of application No. 08/768,622, filed on Dec. 18, 1996, now Pat. No. 6,143,295.

(30) Foreign Application Priority Data

May 10, 1995 (DE) ......................................... 195 17 020
May 7, 1996 (WO) ............................... PCT/EP96/01886

(51) Int. Cl.$^7$ ......................... C12P 21/04; A61K 35/00; A61K 38/00; C12N 1/00
(52) U.S. Cl. ....................... 435/71.1; 424/115; 424/123; 424/93.51; 424/780; 435/942; 435/255.2; 435/940; 514/2; 514/12
(58) Field of Search ...................... 514/2, 12; 435/71.1, 435/255.2, 940, 942; 424/115, 123, 780, 93.51

(56) References Cited

U.S. PATENT DOCUMENTS 3,929,578 A * 12/1975 Urakami ..................... 435/247
4,409,246 A * 10/1983 Stewart et al. ........... 435/255.2
4,797,359 A * 1/1989 Finkelstein ................... 435/68
6,013,485 A * 1/2000 Jaeger ....................... 435/71.1

FOREIGN PATENT DOCUMENTS

CA        1179957    * 5/1982
EP        0286033    * 10/1988

OTHER PUBLICATIONS

Miller et al. Proc. Natl. Acad. Sci. USA, vol. 76, No. 10, pp. 5222–5225, 1979.*
Gropper et al. Exp. Myc., vol. 17, pp. 46–54, 1993.*
Barnes et al. J. Bacteriol., vol. 169, No. 12, pp. 5622–5625, 1987.*
Reading et al. Nature, vol. 337, pp. 655–659, 1989.*
Nicole et al., Methods in Enzymology, vol. 194, "Guide to Yeast Genetics and Molecular Biology", pp. 3638, 3717 (1989).
Barnes et al., "Production of Heat Shock . . . cerevisiae", Journal of Bacteriology, Dec. 1987, pp. 5633–5625.
Gropper et al., "Inhibitors . . . Saccharomyces cerevisiae", Experimental Mycology 17, pp. 46–54 (1993).
Loppnow et al., "IL–1 Induction–Capacity . . . Structures", The Journal of Immunology, vol. 142, pp. 3229–3238, No. 9, May 1, 1989.
Miller et al., "A response of Protein . . . Saccharomyces cerevisiae", Proc. Nat'l. Acad. Sci., USA, vol. 76, No. 10, pp. 5222–5225, Oct. 1979.
Loppnow et al., "[1]Induction of cytokines . . . Products", Methods in Enzymology, vol. 236, pp. 3–10.
Jaffe et al., "Culture of Human Endothelial Cells Derived from Umbilical Veins", The Journal of Clinical Investigation, vol. 52, Nov. 1973, pp. 2745–2756.
Ross et al., "Morphogenesis of Vascular Smooth Muscle in . . . Culture", Chapter 3, pp. 69–91.
Loppnow et al., "Adult Human . . . IL1", Cellular Immunology 122, pp. 493–503 (1989).
Loppnow et al., "Proliferating of Interleukin . . . Interleukin 6", J. Clin. Invest., vol. 85, Mar. 1990, pp. 731–738.
Loppnow t al., "Functional Significance . . . Pathways", Experimental Cell Research 198, pp. 283–290 (1992).
Gillis et al., ". . . Cell Growth Factor: Parameters . . . Activity", The Journal of Immunology, vol. 120, No. 6, pp. 2027–2032, Jun. 1978.
Van Snick et al., "Purification and . . . Hybridomas", Proc. Nat'l Acad. Sci. USA, vol. 83, pp. 9679–9683, Dec. 1986.

* cited by examiner

*Primary Examiner*—Christopher R. Tate
(74) *Attorney, Agent, or Firm*—Pillsbury Winthrop LLP

(57) ABSTRACT

The invention relates to low-molecular weight, metabolism-activating mixtures of active ingredients from yeast fungi of the order Saccharomycetes and is characterized in that they are obtained from yeasts of the said order of Saccharomycetes, which are cultivated for some hours at temperatures starting at 37° C., are heated to a maximum of 45° C. and, following cooling, are subsequently processed in a manner known per se.

12 Claims, No Drawings

LOW-MOLECULAR ACTIVE WEIGHT INGREDIENT EXTRACT FROM YEASTS AND METHOD FOR PRODUCING IT

This is a continuation of application Ser. No. 08/768,622, filed Dec. 18, 1996, now U.S. Pat. No. 6,143,295.

The invention relates to low-molecular weight active ingredients from yeasts and to a method for producing same.

Yeast extracts from fungi in the yeast morphology of the order Saccharomycetes, as well as their anabolic and respiration-stimulating and generally metabolism-activating effects, are known. Methods for obtaining such extracts have been described, for example, in EP-B 0 065 246. In this method, after a proteolytic enzyme had been added at the time of optimum fermentation, a suspension of the yeast is subjected to an ultrasonic treatment until the temperature had been noticeably increased. Although the use of ultrasonics for the dialysis of yeast cells is an effective means for obtaining the extracts, it has been found that the ultrasonic treatment has quite negative side effects, since practically all compounds in an aqueous solution are subjected to a more or less pronounced oxidation. Thus, no genuine active agents are extracted from the cells in the course of the treatment with ultrasonics. Instead, as a rule they are chemically altered compounds.

There is still a demand for yeast extracts and methods for producing them, which result in as genuine as possible a product and have the lowest possible content of substances altered by the production method.

To attain this object, yeast extracts in accordance with claim 1 are proposed, as well as methods for their production in accordance with claim 2.

It has been surprisingly found that it is possible to produce yeast extracts with metabolism-activating effects in a qualitatively and quantitatively improved form, if the cultures are subjected in a defined manner to a temperature change. In accordance with the invention the yeasts, which are maintained at approximately 15° C. prior to preparing the culture, are suspended in water, wherein the ratio of yeast : water is approximately 1:2. Subsequently an amount of sugar, in particular saccharose, which can be fermented with the respective yeast, is admixed in amounts of 5 weight-%. The mass is then heated to the optimum cultivation temperature of 37° to 38° C. and maintained at this temperature for at least 3 hours, and brief stirring and aerating is performed at set intervals. This generation time of the yeasts is approximately 60 minutes.

After three hours of cultivation, the mass then is heated relatively quickly to maximally 45° C. and maintained at that temperature for 60 minutes. Subsequently the suspension is allowed to slowly cool to 25° C. during a period of 60 minutes and is maintained at this temperature for approximately 60 minutes. Thus the total time of the production process lasts approximately 6 hours.

The temperature resistance of the yeasts is improved by increasing the cultivation temperature to a maximum of 45° C. during a generation time, and the total metabolism is clearly increased. It is assumed that the increased yield of low-molecular weight, metabolism-active ingredients is the result of the increased metabolic activity during the increased growth temperature. This assumption is supported in that heat shock proteins can be found in the active ingredient concentrate. Heat shock proteins, hsp for short, are proteins which are briefly synthesized at greatly increased rates by living cells during thermal or chemical stress. Their exact function is not yet known, but they are essential for surviving stress situations, and it is suspected that they initiate or support the ATP-dependent refolding of denatured proteins. Proteins of the hsp family 60 and 70 are contained in the yeasts hydrolyzates. Isolation and proof of hsp are described, for example, in Nature (London) 337, 655 to 659 and 44 to 47 (1989).

*Saccharomyces cerevisiae* also in various pure culture forms, or *Saccharomyces uvarum* or *Saccharomyces rosei*, are preferably used as the yeasts.

Following the approximately total culture time of 6 hours, the mass is comminuted with the aid of suitable mechanical mills, such as colloid mills. If necessary, comminution can also be performed following the enzyme addition. Then the mass is reacted at approximately 37° to 38° C. with a proteolytic enzyme or a mixture of such enzymes, wherein the ratio of enzyme : biomass should be approximately 0.03:1. The reaction time is a function of the type of proteolytic enzyme used and as a rule is approximately 180 minutes. Papain, ficine or bacterial or fungal proteases are preferably employed.

Following solubilization, the entire suspension is heated inside of 30 minutes to 85° C. for activating the enzyme, and is maintained at this temperature for 30 minutes. After cooling, the mass is centrifuged, wherein the sediment can be washed one more time if required. The residue containing the active ingredients sought is filtered and concentrated at temperatures not above 40° C. in vacuo. Subsequently this solution can be subjected to usual and known spray-drying granulation.

The mixtures of active ingredients in accordance with the invention present clearly elevated metabolic activities in comparison with the mixtures of active ingredients known so far and produced in accordance with other methods, which, in the fibroblast test, as a rule are clearly higher, in part by 50 to 100%, than those of the products known up to now.

The mixtures of active ingredients in accordance with the invention can be employed in human medicine and veterinary medicine in all those cases in which an activation of the metabolism is necessary, for example for encouraging the healing of slow-healing wounds, for improved utilization of food, in particular in stock-breeding and pisciculture. A further area of use is in the field of stimulating the activities of microorganisms in enzymatic processes when treating foodstuffs.

The invention will be described in detail below by means of an example:

10 kg of *Saccharomyces cerevisiae* of the bottom yeast culture type are reacted with 20 kg of purified and filtered water of drinking water quality in a reactor. This suspension is provided with 5 weight-% of saccharose and well mixed by stirring. Then the suspension is heated to 37° to 38° C. and maintained at this temperature for at least 3 hours, wherein brief stirring and aeration is performed at intervals of approximately half an hour. Following this the mass is heated to 45° C. and maintained for 60 minutes at this temperature, and afterwards again cooled to 25 over a period of time to 60 minutes and maintained there for 60 minutes.

Subsequently the balanced suspension is reacted with an appropriate amount of papain, wherein the ratio of enzyme biomass should be 0.003:1. Following the enzyme addition with simultaneous comminution of the yeasts, the mixture is stirred for 180 minutes at 37° to 38° C. Then the mixture is heated to 85° C. within 30 minutes and maintained at this temperature for 30 minutes, and then cooled and centrifuged. The centrifuged material is drawn off and the sediment is washed again, and again centrifuged. The centrifuged materials are combined and then, following filtration, concentrated at temperatures below 40° C., preferably with the aid of a vacuum evaporator. The concentrated solution which is free of cells is then subjected in a manner known per se to spray-drying granulation.

What is claimed is:

1. A method for producing a mixture of metabolically active ingredients and heat shock proteins, by:
   (a) cultivating live Saccharomycetes yeast at a temperature between 37–38° C., the yeast being capable of producing heat shock proteins when subjected to stress,
   (b) subsequently heating the yeast to about 45° C., thereby stressing the yeast,
   (c) slowly cooling the yeast to 25° C., and
   (d) isolating from the yeast a mixture of metabolically active ingredients and heat shock proteins,
   wherein the yeast remains viable and intact throughout steps (a), (b) and (c).

2. The method according to claim 1, wherein in step (a) the yeast is cultivated at a temperature between 37–38° C. for 2–6 hours, in step (b) the yeast is heated to 45° C. for 40–80 minutes, and in step (c) the yeast is cooled to 25° C. within 40–80 minutes, and is maintained at 25° C. for about 40–80 minutes.

3. The method according to claim 1 or 2, wherein step (a) further includes adding a fermentable sugar in amount of 5%.

4. The method according to claim 1 or 2, wherein step (d) includes comminuting and enzymatically solubilizing the yeast in the presence of at least one proteolytic enzyme at a temperature of 37°–38° C., heating the yeast to a temperature above 80° C. to effect activation of the at least one proteolytic enzyme, centrifuging the yeast, and isolating a mixture of metabolically active ingredients and heat shock proteins therefrom.

5. The method according to claim 4, wherein the at least one proteolytic enzyme is selected from the group consisting of papain, ficine, bacterial protease and fungal protease.

6. The method according to claim 5, wherein the at least one proteolytic enzyme is papain.

7. The method according to claim 4, wherein proteolytic enzymes are present in step (d) in a ratio with respect to yeast of approximately 0.003:1, by weight.

8. The method according to claim 4, wherein the yeast is *Saccharomyces cerevisiae*.

9. The method according to claim 1, wherein in step (a) the yeast is cultivated at a temperature between 37–38° C. for 2–6 hours.

10. The method according to claim 1, wherein in step (b) the yeast is heated to 45° C. for 40–80 minutes.

11. The method according to claim 1, wherein in step (c) the yeast is cooled to 25° C. for 40–80 minutes.

12. The method according to claim 1, wherein the Saccharomycetes yeast is selected from the group consisting of *Saccharomyces cerevisiae, Saccharamyces uvarum* and *Saccharomyces rosei*.

* * * * *